United States Patent
Yano et al.

(10) Patent No.: US 8,221,604 B2
(45) Date of Patent: Jul. 17, 2012

(54) METHOD FOR CONTROLLING SUBSTANCE TRANSFER

(75) Inventors: Kazuyoshi Yano, Setagaya-ku (JP); Isao Karube, Yokohama (JP); Atsunori Hiratsuka, Sagamihara (JP); Shuo-Wen Tsai, Tsuchiura (JP)

(73) Assignee: Katayanagi Institute, Tokyo (JP)

( * ) Notice: Subject to any disclaimer, the term of this patent is extended or adjusted under 35 U.S.C. 154(b) by 1180 days.

(21) Appl. No.: 10/533,015

(22) PCT Filed: Oct. 28, 2003

(86) PCT No.: PCT/JP03/13768
§ 371 (c)(1),
(2), (4) Date: Jan. 30, 2006

(87) PCT Pub. No.: WO2004/038399
PCT Pub. Date: May 6, 2004

(65) Prior Publication Data
US 2006/0137983 A1    Jun. 29, 2006

(30) Foreign Application Priority Data
Oct. 28, 2002    (JP) ................................ 2002-313534

(51) Int. Cl.
*G01N 27/447* (2006.01)
(52) U.S. Cl. ......... 204/451; 204/450; 204/600; 204/601
(58) Field of Classification Search .................. 204/450, 204/451, 456, 459, 518, 548, 600, 601, 606, 204/610, 616, 627, 644, 660
See application file for complete search history.

(56) References Cited

U.S. PATENT DOCUMENTS

| 4,666,581 A | 5/1987 | Itoh et al. |
| 4,676,274 A * | 6/1987 | Brown ........................... 137/806 |
| 4,874,490 A * | 10/1989 | Hochstrasser ................ 204/467 |
| 6,090,251 A * | 7/2000 | Sundberg et al. ............. 204/453 |
| 2002/0170825 A1* | 11/2002 | Lee et al. ....................... 204/455 |

FOREIGN PATENT DOCUMENTS

| JP | 58-193446 A | 11/1983 |
| JP | 60-236057   | 11/1985 |
| JP | 61-288148 A | 12/1986 |
| JP | 2 151758 A  | 6/1990  |

(Continued)

OTHER PUBLICATIONS

Cheng, Jing, et al., "Preparation and hybridization analysis of DNA/RNA from *E. coli* on microfabricated bioelectronic chips", *Research*, vol. 16, Nature Publishing Group, pp. 541-546, 1998.

(Continued)

*Primary Examiner* — Kaj K Olsen
(74) *Attorney, Agent, or Firm* — Hamilton, Brook, Smith & Reynolds, P.C.

(57) ABSTRACT

Transfer of fluid substances, and/or substances comprised in fluid substances, is controlled by introducing a separation medium, which prevents transfer of the fluid substances, and/or the substances comprised in the fluid substances, to an intermediate cavity connecting a first cavity and a second cavity; and introducing a connection medium to replace the separation medium and thereby start substance transfer to the second cavity. Substance transfer may be readily controlled without relying on mechanical means. Based on the present invention, two-dimensional electrophoretic analysis can be readily implemented on a chip.

12 Claims, 3 Drawing Sheets

FOREIGN PATENT DOCUMENTS

| | | |
|---|---|---|
| JP | 02-309249 | 12/1990 |
| JP | 7-18840 | 3/1995 |
| JP | 2701943 | 10/1997 |
| JP | 11-30605 | 2/1999 |
| JP | 3042774 | 3/2000 |
| JP | 2004 510168 | 4/2004 |
| WO | WO 00/52458 A1 | 9/2000 |
| WO | WO 02/26773 | 4/2002 |

OTHER PUBLICATIONS

Harrison, D. Jed, et al., "Micromachining a Miniaturized Capillary Electrophoresis-Based Chemical Analysis System on a Chip", *Reports*, vol. 261, Science, pp. 895-897, 1993.

Kahn, Patricia, "From Genome to Proteome: Looking at a Cell's Proteins", *Molecular Biology*, vol. 270, Science, pp. 369-370, 1995.

O'Farrell, Patrick H., "High Resolution Two-Dimensional Electrophoresis of Proteins", vol. 250, No. 10, The Journal of Biological Chemistry, pp. 4007-4021, 1975.

Paegel, Brian M., et al., "Microfabricated Capillary Array Electrophoresis: High-Throughput DNA Sequencing and Polymorphism Analysis," Micro Total Analysis Systems, pp. 462-464 (2001).

Rocklin, Roy D., et al., "A Microfabricated Fluidic Device for Performing Two-Dimensional Liquid-Phase Separations," *Anal. Chem.*, 72:5244-5249 (2000).

Chen, Xiaoxi, et al., "A Prototype Two-Dimensional Capillary Electrophoresis System Fabricated in Poly(dimethylsiloxane)," *Anal. Chem.*, 74:1772-1778 (2002).

\* cited by examiner

METHOD FOR CONTROLLING SUBSTANCE TRANSFER

RELATED APPLICATIONS

This application is the U.S. National Stage of International Application No. PCT/JP2003/013768, filed Oct. 28, 2003, published in Japanese, and claims priority under 35 U.S.C. §119 or 365 to Japan Application No. 2002-313534, filed Oct. 28, 2002.

TECHNICAL FIELD

This invention relates to the controlling of substance transfer.

BACKGROUND ART

Material transfer is required in various situations. In particular, substance transfer techniques often become a significant challenge when mechanically reproducing manual operations. For example, biological or chemical experiments are made up of basic operations, such as mixing, reacting, and separating substances. Automation of such operations require a combination of various substance transfer techniques.

In the field of analytical chemistry, microchips have been receiving attention. A microchip is a device wherein substances can be reacted and separated in flow channels formed on glass or plastic surfaces. Microchannels with widths and depths in the range of several micrometers to several hundred micrometers are formed on the microchip. These microchannels are used as cavities for reaction and separation. The use of such cavities, which have minute internal volumes, is a characteristic microchip feature.

Microchannels not only have a reduced internal volume, but also enable transfer of liquids by electroosmosis. Electroosmosis is a phenomenon that takes place on a glass surface or the like which comprises silanol groups (—SiOH), whereby a solvent to which voltage is applied moves toward the cathode. The solvent flow caused by electroosmosis is called electroosmotic flow. On a microchip, solvent can be transported using electroosmotic flow as the driving force, without using a pump or other means of transport.

Due to the above characteristics, microchips are expected to have the following advantages:

The device size itself is small;

The amount of sample required for analysis or separation is small;

Since the amount of sample is small, the period required for reaction, separation, and analysis is short;

The device can be produced inexpensively using a replica; and

Solvent transport is possible independent of mechanical means, such as pumps or valves.

There are many reports of using these advantages in the application of microchips to protein or nucleic acid separation, analysis, and reaction. One such microchip already in practical use is a microchip for electrophoresis.

For example, the Microchip Electrophoresis System "MCE-2010" (Shimadzu Corporation) uses a microchip comprising channels with widths and depths of 10 μm to 100 μm, formed on quartz glass. This microchip is equipped with electrodes necessary for electrophoresis, and also with a hole for supplying electrophoretic buffer, and a slit for optical detection. The channels formed on the microchip function as cavities for electrophoretic separation, as well as channels for supplying sample and electrophoretic buffer from the exterior of the device.

Also known is a microchip for electrophoresis, which uses a number of channels, concentrically located on a circular substrate (Non-patent document 1: Paegel B. M. et al., Proc. of μTAS2001: 462-464, 2001). Since a circular substrate is used, all channels can be optically scanned by rotating the substrate.

In these known microchips, electrophoretic separation is conducted within one continuous channel. Such a structure is not problematic, as long as the electrophoretic separation uses a single medium. However, it is difficult to use this same microchip structure in the continuous electrophoretic separation of combinations of different media.

Generally, physical barriers such as valves or walls for controlling liquid flow cannot be provided in the channels of a microchip. Accordingly, a number of intersecting channels have been used on microchips in an attempt to control the timing of contacting different liquids (Non-patent document 2: Roy D. et al., Anal. Chem. 2000 72, p 5244-5249). When the channels intersect, the timing of contact of different liquids can be controlled by controlling the flow of liquids approaching an intersection. However, such microchips have only one channel for each of the different solvents. As a result, there is a risk that introduction of the second dimensional electrophoretic medium would mix the substances separated by the first dimensional electrophoresis.

Electrophoretic analysis is one analytical technique whose application to microchips has been attempted from an early stage. As mentioned above, microchips for use in electrophoresis are already commercially available. The present inventors have also filed a patent application for an analysis method using two-dimensional electrophoresis, which can be applied to microchips (WO 00/52458). Two-dimensional electrophoresis is important as an analytical technique that provides information extremely important to protein profiling.

In two-dimensional electrophoresis, electrophoresis must be carried out twice, using two different electrophoretic media. For example, two-dimensional electrophoresis using the following combination is common in protein profiling:

First: Isoelectric focusing by capillary gel electrophoresis
Second: Denatured gel electrophoresis using a slab gel Typically, the gel in the capillaries is collected after completion of the first dimensional electrophoresis, and contacted with the slab gel before starting the second dimensional electrophoresis. However, such a procedure is unrealistic on a microchip. Accordingly, a structure was employed comprising a number of cavities branching from the cavity accommodating the first dimensional electrophoretic medium, where the second dimensional electrophoretic medium was placed in these cavities (Patent document 1: WO 00/52458). In this structure, the first and second dimensional electrophoretic media are always in contact during first dimensional electrophoresis. Since an electric drive force is only generated in the first dimensional electrophoretic medium, diffusion of test substances to the second dimensional electrophoretic medium, placed in a branched cavity during the first dimensional electrophoresis, was not deemed a serious problem.

However, in fact there is some possibility that contact of the media for different electrophoreses could vary the electrophoreses conditions. For example, in isoelectric focusing media, the pH gradient has a considerable effect on the electrophoretic analysis results. Accordingly, if the pH of isoelectric focusing media is changed by contact with the second dimensional electrophoretic medium, there is some risk that the isoelectric focusing conditions will change. In other words, during first dimensional electrophoresis, the medium is preferably isolated from the second dimensional electrophoretic medium. However, controlling the timing of media separation and contact is difficult using known microchip structures.

Two-dimensional electrophoresis on a microchip using the principle of capillary electrophoresis has also been attempted (Non-patent document 3: Anal. Chem. 2002, 74, 1772-1778). In this report, however, the top and bottom surfaces of the chip were peeled off after completion of the first dimensional electrophoresis, and the substrate materials for the second dimension were freshly attached to the top and bottom surfaces. In other words, the document does not disclose any specific means for controlling the timing of media separation or contact.

DISCLOSURE OF THE INVENTION

An objective of the present invention is to provide methods for controlling the transfer of fluid substances, and/or substances comprised in fluid substances, whereby the substances are placed in different cavities.

When fluid substances are placed in different cavities, as long as the substances are in contact with each other, it is difficult to avoid diffusion of the fluid substances, or substances comprised in the fluid substances. Accordingly, a mechanical structure for controlling the contact of the fluid substances is generally required. Such mechanical structures use valves, pumps, and barriers that separate the cavities. However, placement of such mechanical structures inside microstructures such as microchips is unrealistic. Further, such placement also leads to sacrifice of the major merit of microchips, which is that transport of liquid is possible without a mechanical structure. The present inventors conducted intensive studies on structures wherein the timing of contact of fluid substances placed in a number of cavities can be controlled without depending on a mechanical structure. Thus, they discovered that the transfer of fluid substances in a number of cavities isolated by an intermediate cavity can be controlled by introducing a medium to the intermediate cavity. The present inventors also discovered that using this technique enables the control of not only fluid substances, but also of substances comprised in the fluid substances, completing the present invention. The present invention relates to methods for controlling fluid substances and/or substances comprised in fluid substances, and devices for realizing such control methods, as described below. The present invention also relates to methods of electrophoretic analysis using such methods, and devices for such methods.

[1] A method for controlling the transfer of a fluid substance and/or a substance comprised in a fluid substance, from the first cavity to the second cavity, comprising the steps of:

a) introducing into the first cavity, a fluid substance whose transfer is to be controlled and/or a substance whose transfer is to be controlled comprised in the fluid substance, and holding the fluid substance and/or the substance comprised in the fluid substance in the first cavity, wherein the first cavity is connected to the second cavity by an into intermediate cavity, and the intermediate cavity is provided with a separation medium which prevents transfer of the fluid substance and/or the substance comprised in the fluid substance into the intermediate cavity;

b) replacing the separation medium in the intermediate cavity with a connection medium that allows transfer of the fluid substance and/or the substance comprised in the fluid substance into the intermediate cavity; and c) transferring the fluid substance and/or the substance comprised in the fluid substance from the first cavity to the second cavity via the intermediate cavity.

[2] The method of [1], wherein one of the following steps (1) to (3) is also carried out in the first and/or second cavity:

(1) separating the fluid substance and/or the substance comprised in the fluid substance;

(2) reacting the fluid substance and/or the substance comprised in the fluid substance; and (3) detecting the fluid substance and/or the substance comprised in the fluid substance.

[3] The method of [2], wherein the separation is carried out by electrophoresis.

[4] The method of [1], wherein the first cavity, the second cavity, and the intermediate cavity comprise a groove or tube configuration; the fluid substance is a liquid; the separation medium is a gas; and the connection medium is liquid.

[5] The method of [4], wherein the second cavity comprises the form of at least one groove or tube that branches from the first cavity.

[6] A device for controlling the transfer of a fluid substance and/or a substance comprised in a fluid substance, comprising:

a) a first cavity for holding the fluid substance;

b) a second cavity for holding the fluid substance; and c) an intermediate cavity for connecting the first cavity and the second cavity, for holding a separation medium which prevents transfer of the fluid substance and/or the substance comprised in the fluid substance from the first cavity;

wherein the separation medium can be replaced with a connection medium, and the introduction of the connection medium to the intermediate cavity enables transfer of the fluid substance and/or the substance comprised in the fluid substance retained in the first cavity to the intermediate cavity and the second cavity.

[7] The device of [6], wherein the first cavity and/or the second cavity comprises at least one of the following mechanisms (1) to (3):

(1) a mechanism for separating the fluid substance and/or the substance comprised in the fluid substance;

(2) a mechanism for reacting the fluid substance and/or the substance comprised in the fluid substance; and (3) a mechanism for detecting the fluid substance and/or the substance comprised in the fluid substance.

[8] A two-dimensional electrophoretic device comprising:

a) a first cavity for holding an electrophoretic medium;

b) a second cavity for holding an electrophoretic medium; and c) an intermediate cavity for connecting the first cavity and the second cavity, for holding a separation medium which prevents transfer of the substance to be electrophoresed from the first electrophoretic medium to the second electrophoretic medium;

wherein the separation medium can be replaced with a connection medium, and the introduction of the connection medium to the intermediate cavity enables transfer of the substance to be electrophoresed in the electrophoretic medium retained in the first cavity to the intermediate cavity and the second cavity.

[9] The two-dimensional electrophoretic device of [8], wherein the second cavity comprises the form of at least one groove or tube that branches from the first cavity.

[10] A method for conducting two-dimensional electrophoresis comprising the steps of:
   a) conducting electrophoresis in the first cavity of the electrophoretic device of [8];
   b) introducing a connection medium to an intermediate cavity after step a); and
   c) conducting electrophoresis of a substance to be electrophoresed in the second cavity.

The present invention relates to a method for controlling the transfer from a first cavity to a second cavity of a fluid substance and/or a substance comprised in a fluid substance, comprising the steps of:
   a) introducing into the first cavity a fluid substance whose transfer is to be controlled, and/or a substance whose transfer is to be controlled comprised in the fluid substance, and holding the fluid substance and/or the substance comprised in the fluid substance in the first cavity, wherein the first cavity is connected to the second cavity by an intermediate cavity, and the intermediate cavity is provided with a separation medium which prevents transfer of the fluid substance and/or the substance comprised in the fluid substance into the intermediate cavity;
   b) replacing the separation medium in the intermediate cavity with a connection medium that allows transfer of the fluid substance and/or the substance comprised in the fluid substance into the intermediate cavity; and
   c) transferring the fluid substance and/or the substance included in the fluid substance from the first cavity to the second cavity via the intermediate cavity.

In the present invention, the first and second cavities may be of any structure, as long as they can retain fluid substances, and of any configuration suited to the handling of fluid substances. Therefore, the first and second cavities may either be closed or open systems. Preferable forms of the first and second cavities of the present invention include, for example, tubes, grooves, and combinations of tubes and grooves. The combinations of tubes and grooves refer to structures in which the tubes and grooves are arranged in series.

The supports forming the first and second cavities are composed of material that can hold fluids. Further, when treating fluid substances in these cavities, materials suited to such treatments are selected. For example, glass or plastic, which is inert to many substances, can be used as a support in chemical reactions, biological reactions, electrophoresis, and other processes. The use of glass is particularly preferable in electrophoresis, since an electroosmotic flow can be generated by applying voltage.

In the present invention, the support may also comprise surface-modified materials. For example, the surface hydrophilicity of synthetic resin or glass can be adjusted by plasma treating the surface. Alternatively, the support surface can be modified by coating it with an arbitrary polymer. Affinity for the fluid substance, or affinity for substances contained in the fluid substance, can be adjusted by the choice of polymer material coating the surface.

The support forming the first and second cavities of the present invention is preferably integrated. "Integration" means that the support forming each cavity is continuous. Accordingly, integrated supports include not only supports comprising a single material, but also supports constituted by connecting a number of components. For example, a closed-up structure in which grooves on the surface of the first substrate material are covered with a second substrate material, can be indicated as an integrated support of the present invention. A hole that leads to a groove may be provided in the second substrate material, and fluid or samples can be supplied. Furthermore, the hole provided in the second substrate material may also serve as a reservoir for holding fluid or samples.

When the support is constructed by connecting a number of components, the components are preferably connected such that each component can not be easily detached. Specifically, structures preferred in the present invention include supports connected by means such as adhesion, fusion, screwing, and fitting. For example, a number of grooves may be formed on the surface of one planar support, and each of the grooves may be used as a first or a second cavity.

The width of the grooves holding electrophoretic medium can be cavities as fine as 1 to 100 µm wide. Groove cross-sections can be polygonal, such as triangular and square, or U-shaped and semicircular. Such finely structured grooves can be provided on a support such as glass using the following methods:
   wet etching methods in semiconductor processing technique (methods using hydrofluoric acid),
   dry etching methods in semiconductor processing technique (ion spattering, reactive ion etching (ICP etching, etc.)),
   laser boring methods, and
   dicing saw methods.

Microstructures of any shape can be readily provided by using techniques such as wet etching, dry etching, and laser boring. For example, grooves with widths and depths from 10 to 100 µm can be provided on a glass surface by known techniques. The present inventors have also succeeded in producing a microchannel by using reactive ion etching. In the reports of the present inventors, etching with good selectivity and a high etching rate is made possible by using different types of etching gas according to the type of substrate material.

The number of the first and second cavities in the present invention is not limited, and one or more first cavities can be combined with one or more second cavities.

Also, the number of sets of first and second cavities is not limited in the present invention. Thus, a number of sets may be provided on the same support. More specifically, a number of sets each comprising one first cavity and a number of second cavities can be provided on a single support. Each set may be provided to constitute a cavity independent from other sets. Alternatively, the sets may be constituted to allow transfer of fluid substances and/or substances comprised in the fluid substances between different sets.

The first and second cavities of the present invention are relative to each other. More specifically, the first cavity holds the substance to be transferred, and the second cavity receives the transferred substance. Accordingly, when a number of sets (each comprising first and second cavities) interact with each other, a first cavity of one set may receive substance from a second cavity of another set. In other words, a second cavity may function as a first cavity for cavities in other sets.

In the present invention, an intermediate cavity is provided between the first and the second cavities, such that the intermediate cavity connects the two cavities. Transfer of fluid substances and/or substances comprised in the fluid substances from the first cavity to the second cavity may be restricted by placing a separation medium in the intermediate cavity. A separation medium of the present invention is a medium comprising the function of preventing transfer to the intermediate cavity of either one or both of the fluid substances, and the substances comprised in the fluid substances, which are accommodated in the first cavity. The term "substances to be transferred" is hereinafter used to represent one or both of the fluid substance, and substances comprised in the fluid substance, accommodated in a first cavity of the present invention.

Gas or liquid may be used as a separation medium. For example, when the first cavity holds aqueous media, transfer of the aqueous media to an intermediate cavity can be restricted by filling the intermediate cavity with air. One example of a basic structure for carrying out the control methods of the present invention can be a structure whereby the first cavity comprises one groove, the second cavity comprises a second groove that intersects the first cavity, and the intermediate cavity comprises a third groove that intersects the second cavity groove. The third groove is located near the intersection of the first and second cavities. In this structure, the liquid accommodated in the first cavity can not be transferred to the second cavity without passing through the intermediate cavity (third groove). When air is present in the intermediate cavity, the surface tension of the aqueous medium in the first cavity (the first groove) prevents this aqueous medium from entering the intermediate cavity. As a result, the transfer of the aqueous medium in the first cavity is controlled.

The connection medium of the present invention is a medium which, upon contact with the "substances to be transferred", enables the transfer of this substance to the second cavity. When the substances to be transferred is a fluid substance, liquid miscible with the fluid substance can be used as the connection medium. The fluid substance is transferred to the second cavity through the connection medium in the intermediate cavity, by physical energy such as diffusion into the miscible liquid, electroosmotic flow, centrifugal force, or the like. When the substance to be transferred is a substance comprised in the fluid substance, it can be transferred to the second cavity through the connection medium in the intermediate cavity by diffusion or electricity.

When the substance to be transferred, which is accommodated in the first cavity, is a liquid, the separation medium may be a liquid immiscible with this material. By introducing the intermediate cavity with a miscible liquid connection medium instead of an immiscible liquid, the substance to be transferred can be guided into the intermediate cavity.

The number of intermediate cavities is not limited in the present invention. The present invention controls the transfer of a substance to be transferred in the first cavity, by selecting which separation media and connection media is placed in the intermediate cavity. Accordingly, by increasing the number of intermediate cavities, the number of steps controlling the substance to be transferred can be increased. More specifically, one intermediate cavity can control the transfer of the substance to be transferred at least once. When a number of second cavities are connected to the first cavity, transfer of the substance to be transferred to the multiple second cavities can be started at once, by providing one intermediate cavity.

Figure 1:
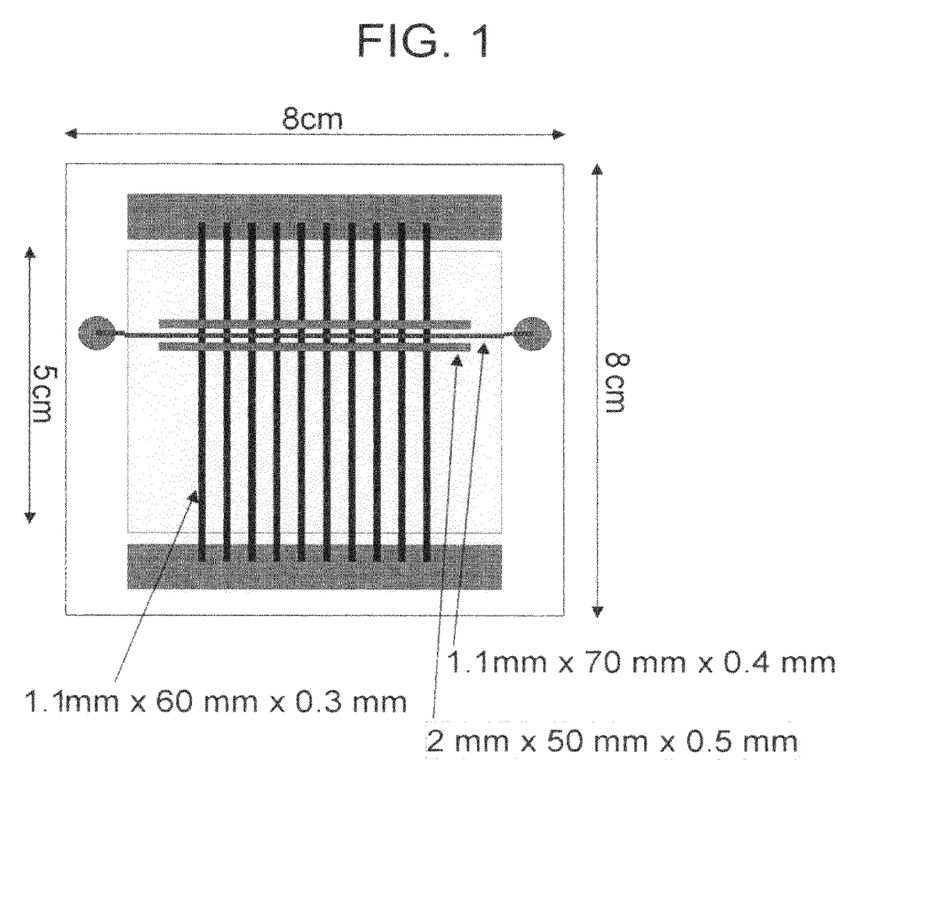
FIG. 1 is a diagram showing the structure of the two-dimensional electrophoretic device produced in the Example.

FIG. 1 shows an example of such a structure. As shown in FIG. 1, provision of two intermediate cavities intersecting a number of second cavities enables simultaneous control of the transfer of a substance to be transferred to a number of second cavities. Alternatively, a number of intermediate cavities can be provided for a number of second cavities, to independently control each intermediate cavity. For example, all second cavities may be separately provided with an intermediate cavity, to thereby independently control transfer of the substance to be transferred to all second cavities. This independent provision of intermediate cavities prevents mixing of the substance to be transferred through the intermediate cavity.

The second cavities of the present invention may or may not comprise a fluid substance prior to receiving the substance to be transferred. When a fluid substance is present in the second cavity, it is desirable to restrict the transfer to the first cavity of fluid substances and/or substances comprised in the fluid substances in the second cavity, through the separation medium.

The substance transfer methods of the present invention can be used in reactions between substances, separation of substances, or detection of substances. To realize such applications, fluid substances, and/or substances comprised in the fluid substances, can be handled in the first cavity and/or second cavity under various conditions. In the present invention, the handling of fluid substances, and/or substances comprised in the fluid substances, comprises using such substances in reactions, separating, detecting, and imparting other substances or varieties of energy to such substance. Specific examples of such treatments are given below.

Using the Substances in a Reaction

The fluid substances and/or substances comprised in the fluid substances can be used in various reactions, including enzymatic reactions, chemical reactions, biological reactions, and electrochemical reactions. Any one of, or a number of such reactions can be performed in the first or second cavity.

Separating the Substances

The fluid substances and/or substances comprised in the fluid substances can be separated. In the present invention, separation refers to physical separation using a phenomenon wherein some driving force moves a substance in a medium. Exemplary driving forces include voltage, centrifugal force, capillarity, magnetic force, electroosmotic flow, and pumping. Electrophoresis using voltage is a drive principle widely used for two-dimensional electrophoresis. Separation includes separation methods based on various electrophoreses, gel filtration, affinity chromatographies, and other principles. Any or a number of such separation steps can be conducted in the first or second cavities.

Detecting Substances

The fluid substances, and/or substances comprised in the fluid substances, can be detected. Detection comprises detection techniques based on optical, electrical and physical principles. Any or a number of detection methods based on these principals can be conducted in the first or second cavities.

Imparting the Action of Other Substances or Various Energies to the Substance

The effect of another substance or various energies may be imparted to the fluid substances and/or substances comprised in the fluid substances. An action of another substance is, for example, adding a substance to the cavity from outside the cavity. Alternatively, various energies may be imparted by heating or cooling the substance in the cavity, or by irradiating with light, electromagnetic waves, or other radiation. The effects of these substances or energies may be imparted in the first or second cavities.

In the present invention, the treatments described above may be arbitrarily combined. For example, a reaction may be conducted in the first cavity, and a separation and detection may be conducted in the second cavity. More specifically, an enzymatic reaction such as PCR may be carried out in the first cavity, and the reaction results may be analyzed after introducing a reaction solution to the second cavity.

The methods for controlling substance transfer of the present invention may be carried out by a device with the structure below. In other words, the present invention relates to devices for controlling the transfer of fluid substances and/or substances comprised in the fluid substances, comprising the components described below. Please note the specific structures of the first, second, and intermediate cavities constituting the devices of the present invention are as described above.

a) a first cavity for holding a fluid substance;
b) a second cavity for holding a fluid substance; and
c) an intermediate cavity for connecting the first and second cavity, and for holding a separation medium which prevents the inflow of fluid substances and/or substances comprised in the fluid substances from the first cavity;
wherein the separation medium can be replaced with a connection medium, and the introduction of the connection medium to the intermediate enables transfer of fluid substances and/or substances comprised in the fluid substances in the first cavity to the intermediate cavity and the second cavity.

In a first and/or second cavity, a device of the present invention may further comprise at least one of the following mechanisms (1) to (3):
(1) a mechanism for separating the fluid substance and/or the substance comprised in the fluid substance;
(2) a mechanism for reacting the fluid substance and/or the substance comprised in the fluid substance; and
(3) a mechanism for detecting the fluid substance and/or the substance comprised in the fluid substance.

These mechanisms are for performing various treatments that may be conducted in the first and second cavities. For example, the separation of the aforementioned fluid substances and/or substances comprised in the fluid substances includes mechanisms such as electrodes for electrophoresis, or rotational mechanisms for centrifugal separation. Examples of mechanisms for reacting the fluid substances and/or substances comprised in the fluid substances include mechanisms for temperature control and for reagent addition. Examples of mechanisms for detecting the fluid substances and/or the substances comprised in the fluid substances include sensors for detecting luminescence and fluorescence, and for measuring absorption.

Exemplary combinations of treatments of the present invention comprise electrophoretic analyses based on different drive principles, generally referred to as "two-dimensional electrophoresis". In two-dimensional electrophoresis, separation is carried out from two aspects of substances, and thus a drastic improvement in resolution can be expected. In two-dimensional electrophoresis, for example, electrophoresis based on isoelectric points is carried out, and then electrophoresis based on molecular weights is carried out in a different medium (O'Farrell, P. H., J. Biol. Chem. 250, 4007-21, 1975). As a result, substances are two-dimensionally developed based on two different properties: isoelectric point and molecular weight. Therefore, even substances of the same molecular weight can be developed to different coordinates if their isoelectric points are different. That is, each substance can be separated as a spot on two-dimensional coordinates, with isoelectric point on the X axis, and molecular weight on the Y axis. Because of its excellent resolution, two-dimensional electrophoresis is highly estimated as a method for separating proteins in particular.

With the progress of large scale projects to analyze genetic information, such as the Genome Project, a tremendous amount of genetic information has been revealed. From now on, the major challenge is to progress the functional analysis of genes, by elucidating the relationships between the genetic information thus revealed, and the variety of proteins in complicated in vivo interactions.

A novel concept, termed "PROTEOME" as a combination of PROTEin and genOME, has been proposed (Kahn, P., Science 270, 369-70, 1995). Proteome analysis is a novel attempt to systematically comprehend the relationships between the varieties of proteins that support cellular functions. However, the analytical techniques presently available require tremendous amounts of time and labor to analyze proteins, as compared with genes. There are said to be 5000 to 7000 proteins that make up cells. Hence, systematic as well as rapid comprehension of variations in the proteome, which is a collection of these richly diverse proteins, has been sought.

Two-dimensional electrophoresis of proteins plays an important part in achieving this objective. Databases used to compare the developed patterns obtained by two-dimensional electrophoresis with information on identified proteins are significant as so-called protein catalogues. If there was a catalogue of cellular proteins under normal conditions, any cellular mutation could be perceived as a change in the two-dimensional electrophoretic pattern of those proteins. If spots that specifically appear or disappear in the electrophoretic patterns of a protein in a mutated cell can be detected, information critical to surmising the function of that protein can be obtained. This kind of information is not only important to discovering the relationships between cellular functions and the proteins supporting these functions, but can also very probably lead to great achievements in the broad field of bioindustry, such as drug development and the genetic breeding of plants and animals.

Currently, two-dimensional electrophoresis of proteins generally proceeds as below: First, isoelectric focusing (a first dimensional separation) is performed using capillary gels or commercial strip gels as a separation medium. After completing the first dimensional electrophoresis, the gel is mounted on to a second gel for the second dimensional electrophoresis. A slab gel is used since the second gel should be electrophoresed at right angles to the first dimensional developing direction. When isoelectric focusing is used as the first dimensional separation, SDS-polyacrylamide gel electrophoresis (hereafter abbreviated as SDS-PAGE) is generally selected as the second dimensional separation. Using this combination, proteins are separated first-dimensionally based on their isoelectric points (pI), and then developed second-dimensionally based on their molecular weights.

Based on the above methods, two-dimensional electrophoresis has already been performed for many proteomes. The analytical results obtained by amino acid sequencing and peptide mass fingerprinting methods performed on isolated protein spots have been recorded along with coordinate information, and stored in databases such as SWISS-2DPAGE®.

The two-dimensional electrophoresis known in the art is a high resolution separation technique. However, the step of mounting the gel resulting from isoelectric focusing onto the second dimensional electrophoretic medium is a complicated step requiring manual labor. This step has also been a major obstacle in realizing the two-dimensional electrophoresis on the above described microchips. Implementation of electrophoresis on a microchip by parallel use of the second dimensional electrophoretic media has also been reported (WO 00/52458). This structure, however, has not realized a mechanism to block the first dimensional electrophoretic media from the second dimensional electrophoretic media. On the other hand, the methods for transferring substances of the present invention can readily separate the two electrophoretic media, and control transfer of the substance to be electrophoresed.

Two-dimensional electrophoretic analysis according to known techniques required a long time, up to 20 hours, for example.

Accordingly, the present invention provides two-dimensional electrophoretic devices comprising:

a) a first cavity for holding an electrophoretic medium;
b) a second cavity for holding an electrophoretic medium; and
c) an intermediate cavity for connecting the first cavity and the second cavity, and for holding a separation medium which prevents transfer of the substance to be electrophoresed from the first electrophoretic medium to the second electrophoretic medium;
wherein the separation medium can be replaced with a connection medium, and introduction of the connection medium to the intermediate cavity enables transfer of the substance to be electrophoresed, which is in the electrophoretic medium retained in the first cavity, to the intermediate cavity and the second cavity.

In the case of so-called electrophoresis, using voltage as a driving force, the following moving conditions may be provided as examples: pH gradient, molecular sieve, and interaction with functional groups contacted in the electrophoretic medium. Electrophoresis of proteins in a medium with a pH gradient is isoelectric focusing. If protein denaturants such as SDS, urea, or guanidine are also present, electrophoresis performed in a medium with a molecular sieve effect, such as a polyacrylamide gel, establishes molecular sieve electrophoresis under denaturing conditions. Alternatively, in the absence of denaturants, this becomes electrophoresis under native conditions. Furthermore, media with a variety of functional groups can also be used. Specific examples are affinity substances capable of electrostatic interaction, forming hydrogen bonds and hydrophobic bonds, or any desired combinations thereof. Examples also include combinations of affinity substances such as antigen-antibody, hybridization of nucleic acids comprising complementary nucleotide sequences, avidin-biotin, and sugar-lectin. These conditions can be applied to driving forces other than electrophoresis.

Second dimensional separation in the present invention is conducted in the electrophoretic medium in the second cavity, irrespective of the type of drive principle employed. The second cavity is connected to the first cavity via an intermediate cavity. The first and second cavities can be realized, for example, by a structure comprising at least two grooves that branch on a flat plane. In the present invention, a branched structure comprises grooves in the form of a T, Y, or cross, or a structure with a larger number of intersecting grooves. In addition, the structure may comprise a number of second cavities branching from a single first cavity, or a small number of second cavities branching from a number of first cavities.

In performing a separation method of this invention using fine grooves on a support, a first dimensional separation medium can be placed on the same support as a second dimensional separation medium. For example, a groove filled with a first dimensional separation medium is provided along one edge of a support. Then, a number of grooves branching out from this first dimensional groove are provided for use with second dimensional media. The shape of the entire support can be arbitrary, but shapes like squares are preferred for mechanically scanning electrophoretic images. Therefore, second dimensional separation media are preferably designed to branch off from first dimensional separation medium at near right angles. In this embodiment, even though, for example, 100 grooves of width 30 μm are arranged in parallel at intervals of 20 μm for use as second dimensional separation medium, the width required to arrange them in rows is only 5 mm, since each groove to accommodate separation medium is fine. That is, two-dimensional separation can be performed on a tiny 5 mm square support. Namely, this invention realizes square chips of merely 5 mm for use in two-dimensional separation.

Alternatively, a structure can be arranged such that first dimensional separation medium is placed on a concentric circle in the central part of a disciform support, from which a second dimensional medium extends toward the periphery. These chips for two-dimensional separation with this structure enable easy and speedy optical scanning of the entire support by rotating the discal support. Second dimensional separation can also be performed by centrifugal separation using a rotational mechanism.

By using a highly integrated chip, either square or circular, for two-dimensional separation based on this invention, migration distance is shortened and migration time is thus reduced, such that this invention can be expected to provide a dramatic improvement in the throughput of two-dimensional separation along with improved reproducibility. In capillary electrophoresis, the separation medium does not need to be gel, and a liquid medium may be used. In the case where the separation medium is a liquid, this kind of procedure to introduce separation medium in to a capillary can be readily carried out by micropump or electroosmotic flow.

The intermediate cavity can separate the electrophoretic medium in the first cavity from the electrophoretic medium in the second cavity, as well as connect the first cavity with the second cavity. The intermediate cavity can be realized, for example, by a third groove structure intersecting the second cavity branching from the groove that constitutes the first cavity, at a position beyond the branching point of the first and second cavities. For example, assuming that the second grooves constituting the second cavity are placed perpendicular to the first cavity (first groove), a third groove placed along the first groove and intersecting with the second grooves may be provided as the intermediate cavity. The third groove and the first groove do not need to be parallel, as long as they are side by side.

After completing electrophoresis in the first cavity, a connection medium is introduced to the intermediate cavity. The substance separated in the electrophoretic medium in the first cavity (the substance to be electrophoresed) then moves in to the connection medium. The connection medium contacts the electrophoretic medium in the second cavity. Thus, the substance to be electrophoresed can now move into the electrophoretic medium in the second cavity. Electrophoresis of the substance in the second cavity can begin when voltage is applied under these conditions in the axial direction of the second cavity.

Any of the separation principles used in known two-dimensional electrophoreses can be applied to the two-dimensional electrophoretic separation methods of the present invention. Proteins are a representative component for separation by two-dimensional electrophoreses. Protein separation by two-dimensional electrophoresis is generally carried out by a combination of isoelectric focusing in the first dimension, and denatured gel electrophoresis in the second dimension.

In the protein separation by two-dimensional electrophoresis according to the present invention, an isoelectric focusing medium may be filled in the first cavity, and a denatured gel may be filled in the second cavity. In this case, the second cavity may retain a slab gel, or may be in the form of a strip or capillary. When the denatured gel of the second dimension is in the form of a strip or capillary, a number of denatured gels may be provided such that they intersect with the isoelectric focusing medium in the first cavity. Such an arrangement realizes second dimensional development in the strip or capillary gel. The strip or capillary gel may be accommodated in narrow cavities, such as in narrow grooves. The present inventors have already filed a patent application for a technique which realizes second dimensional development in a strip or capillary gel (WO 00/52458).

For example, grooves formed on a flat surface can be used as the first cavity. An attempt to conduct electrophoresis by filling microgrooves provided on the support with separation medium is known (Science Vol. 261, 895-897, 1993). When electrophoresis is conducted within such microcavities, the substance can be expected to develop due to electroosmotic flow. In other words, separation based on similar principles to capillary electrophoresis is possible. When electric current is passed through the interior of a microcavity formed by glass walls, hydrated cations on the surface of the glass move toward the cathode. This can be macroscopically observed as a movement of the medium toward the cathode. This phenomenon is called "electroosmosis", and is significant as a driving force in the development of substance in capillary electrophoresis (Japanese Society of Biochemistry ed., Lectures on Experiments in Biochemistry, New Series, "Proteins: Separation, Purification, Characteristics", page 340, 1990).

Electrophoretic medium with a pH gradient for isoelectric focusing is placed in the grooves. Next, grooves (capillaries) are used as the second cavity to accommodate the denatured gel. As described above, when a number of denatured gels are placed to intersect the isoelectric focusing lane, second dimensional development can be carried out using these grooves. The denatured gels are preferably placed to intersect the isoelectric focusing medium, so that the protein to be electrophoresed, which was received from the isoelectric focusing medium, can be developed in an arbitrary direction. Since this kind of spacial arrangement is composed by grooves formed on a flat surface, arrangements wherein a number of grooves constituting the second cavity intersect with a straight first cavity are possible. Each of the grooves is provided with an electrode for supplying electric current for electrophoresis.

A two-dimensional separating device of this invention is preferably equipped with a temperature controller, so that second dimensional separation media in particular can be maintained under homogeneous temperature conditions. Since a number of electrophoretic media are used in combination in this invention, maintenance of homogeneous conditions among separation media is essential to achieving high reproducibility. When performing second dimensional separation by electrophoresis in particular, temperature control of separation media is highly significant because of the heat generated (Joule heat) by turning the electricity on. A temperature controller can be composed by placing the separation media in a water bath equipped with a thermostat or in a temperature controllable closed cavity. When temperature does not greatly affect separation results, due to the type of driving force or under certain separating conditions, the importance of a temperature controller is diminished.

Two-dimensional separating devices of this invention may be provided with mechanisms for pretreatment, to supply test samples as targets for analysis, and standard samples such as molecular markers. For example, proteome analysis can be automated if a device is provided with a means for mechanically performing steps for isolating cells from a culture, and disintegrating the cells to obtain proteomes. For example, techniques are known in the art wherein bacteria are isolated using a flow cell provided with an agarose layer formed on platinum electrode, and further treated with enzymes to extract nucleic acids thereof (Heller, et. al. Nature Biotechnology 16/6, p 541-6, 1998). Such isolation techniques can be used as pretreatments for the two-dimensional isolating devices of this invention.

In addition, a two-dimensional separating device according to this invention can be installed with a sensor for reading the results of two-dimensional separation. Where the objects to be analyzed are fluorescently labeled proteins, the coordinate information can be mechanically read by scanning the second dimensional separation media with a fluorescence sensor. Alternatively, a means can be incorporated wherein both first and second dimensional separation are carried out, such that the first separation medium is automatically provided to the second dimensional separation medium. The two-dimensional separating devices with such mechanisms of this invention can automate almost all processes required for two-dimensional separation, contributing to dramatically improved efficiency in proteome analysis.

In the present invention, an intermediate cavity is provided between the first and second cavities. For example, as described above, when a third cavity intersecting with a second cavity is placed somewhere between the intersection of the first and second cavities and the second cavity, an intermediate cavity with grooves in the relation described above can be achieved. That is, a third groove serving as the intermediate cavity can be placed to extend along the second cavity and intersect with the second cavity(s).

The distance between the grooves serving as the first and intermediate cavities is arbitrary. When this distance is great, a larger amount of protein in the first cavity may diffuse to the intermediate cavity during isoelectric focusing. Therefore, the distance between these cavities is preferably short. Specifically, the intermediate cavity may be placed at a distance of 10% to 200% of the width of the groove constituting the first cavity.

The number of the grooves constituting the intermediate cavity is not particularly limited. For example, a pair of grooves may be placed on both sides of a first cavity as the intermediate cavity. When such grooves placed on both sides of the first cavity are connected at a position that does not intersect with the first or second cavity, the intermediate cavities will constitute one U-shaped groove. On the other hand, when discontinuous grooves are used as the intermediate cavities, intermediate cavities formed from a number of grooves may be realized.

Separation medium, which prevents the transfer of substance to be electrophoresed, is placed in the intermediate cavity. Exemplary separation media comprise gas such as air. Isoelectric focusing is conducted in the first cavity, with separation medium in the intermediate cavity. During isoelectric focusing, the separation medium prevents diffusion of the substance to be electrophoresed into the denatured gel in the second cavity.

After the completion of isoelectric focusing, connection medium is introduced to the intermediate cavity. A buffer may be used as the connection medium, and specific examples include Tris buffer, phosphate (sodium or potassium) buffer, glycine buffer, carbonate buffer, borate buffer, the Good's buffer series, citrate buffer, phthalate buffer, formate buffer, acetate buffer, succinate buffer, cacodylate buffer, imidazole buffer, and pyrophosphate buffer.

Introduction of a buffer enables diffusion of the substance to be transferred from the first cavity to the intermediate cavity. In this state, application of voltage to the second cavity starts electrophoresis in the second cavity, which is equipped with a denatured gel. More specifically, the substance to be electrophoresed, which was separated in the isoelectric focusing medium, will transfer to the nearest second cavity of each band. Two-dimensional electrophoresis separation methods that use two-dimensional electrophoretic separation devices of the present invention are thereby implemented.

The present invention provides methods for conducting two-dimensional electrophoresis comprising the steps of:
a) conducting electrophoresis in a first cavity of an electrophoretic device as described above;
b) introducing a connection medium to an intermediate cavity after step a); and
c) conducting electrophoresis of the substance to be electrophoresed in a second cavity.

In the present invention, not only proteins, but also other substances like organic substances such as nucleic acids, microorganisms such as bacteria and viruses, animal and plant cells, inorganic ions, and various substances whose use as objects for analysis is known in various analysis techniques, can also be used as objects for analysis. Analysis by two-dimensional electrophoresis is particularly significant when the object for analysis is a protein. Two-dimensional electrophoresis of proteins is currently an important technique in the above-described proteome analysis. The present invention can be applied to proteome analysis using procedures described below.

First, a proteome sample prepared by known procedures is subjected to first dimensional electrophoresis. Generally, two-dimensional electrophoretic analysis of a protein is conducted by isoelectric focusing in the first dimensional electrophoresis, and SDS-PAGE in the second dimensional electrophoresis. Accordingly, separation by isoelectric focusing is conducted in the electrophoretic medium in the first cavity. More specifically, the proteome sample is applied to the center of a medium with a pH gradient, and electrophoresed by passing an electric current through the medium for an adequate time, by immersing the opposite ends of the medium in an anode buffer and cathode buffer for electrophoresis. The proteome sample may be fluorescently labeled prior to electrophoresis. At the same time, isoelectric markers may also be electrophoresed under the same conditions.

After first-dimensional electrophoresis, a connection medium is introduced to the intermediate cavity. A buffer is used as the connection medium. The protein comprised in the first dimensional electrophoretic medium can transfer through the buffer to the denatured gel for SDS-PAGE in the second cavity. SDS-PAGE is conducted at this stage. The individual proteins constituting the proteome developed in the first dimensional gel transfer to the nearest second dimensional gel retained in the second cavity, and are developed according to their molecular weight. Molecular weight markers may also be electrophoresed under the same conditions.

Protein spots are confirmed on gels after completing second dimensional electrophoresis. If the proteins are fluorescently labeled, the spots can be confirmed by monitoring their fluorescence at this time. Protein spots can also be verified by CBB and silver stains. Proteins thus separated can be identified based on coordinate information, by referring to the results of two-dimensional electrophoresis performed under identical conditions as a comparison. Alternatively, to proceed with the analysis of an unknown proteome, the proteins in individual spots are identified.

Proteins are identified based on amino acid sequence analysis and peptide mass-finger print methods. Amino acid sequences can be determined from amino terminals by techniques such as the Edman degradation method. At this stage, the amino acid sequence of the entire protein need not be determined. Even if only partial amino acid sequences are available, this is information critical to enabling protein identification. The N-terminus of many proteins is often blocked, a state unfavorable for sequencing. One technique for accurately sequencing amino acids of this type is a method wherein protein fragments, obtained by digestion with proteases, are sequenced. Although digestion with proteases occurs at a variety of sites depending on the protein, proteins can be identified by checking the partial amino acid sequences thus determined against known amino acid sequence databases.

On the other hand, compared with labor-intensive amino acid sequencing, peptide mass-fingerprinting methods can more speedily provide a variety of information useful for protein identification. Mass patterns (i.e. fingerprints) of the protease-digested fragments are obtained by using a set protease to digest the proteins contained in the spots separated as a result of two-dimensional electrophoresis, and then analyzing the fragments thus obtained using a mass spectrogram. Proteins can be identified based on these peptide mass fingerprints since they are information highly unique to individual proteins, and databases which accumulate such data, such as PROTEINPROSPECTOR®, can be utilized on the Internet.

In proteome analysis, the two-dimensional electrophoretic patterns of proteomes under a variety of conditions are compared, and the ebb and flow of spots related to particular functions are observed. Proteins that make up spots which disappear in the proteomes of cells under particular conditions, or, proteins that make up spots that specifically appear, are highly likely to be involved in functions of interest. If these proteins can be identified based on their partial amino acid sequences and peptide mass finger prints, their relation to functions of interest can be inferred. Alternatively, if a protein is unknown in the field, the genes supporting functions of interest and protein operations can be elucidated by isolating the protein and further cloning the genes that encode the protein, and factors controlling the genes.

This patent application relates to the results of contract research with the government ("Development of technology for analyzing the expression and interaction of proteins" contract research with New Energy and Industrial Technology Development Organization in 1999, pursuant to Article 30 of Law on Special Measures for Industrial Revitalization).

BEST MODE FOR CARRYING OUT THE INVENTION

Example 1

The Structure of the Two-Dimensional Capillary Separation Devices

A two-dimensional capillary electrophoretic device comprising two different separation modes on one support was produced. In this system, isoelectric focusing can be carried out in the first dimension, and capillary zone electrophoresis can be carried out in the second dimension. Proteins are separated by their isoelectric point in the first dimensional capillary, and by their charge and mass in the second dimensional capillary. To achieve a capillary structure that comprises the different modes on one support, the structure described below was produced:

First, a number of second dimensional capillaries (second cavities) were placed to cross one first dimensional capillary (first cavity) at right angles. Next, two capillaries serving as intermediate cavities were produced at the intersection of the first and second dimensional capillaries, parallel to the first dimensional capillary. The capillaries serving as intermediate cavities were placed on both sides of the first dimensional capillary. All capillaries were formed by processing glass substrate materials with a dicing saw. More specifically, grooves of the size described below were formed on the surface of a 3 mm thick, 80 mm×80 mm glass substrate material, and used as capillaries. The first dimensional capillary was placed perpendicular to the second dimensional capillaries, 1.8 mm from one end of the second dimensional capillaries. The distance between the first dimensional capillary and the capillaries serving as intermediate cavities was 2.0 mm. The intermediate cavities were placed on both sides of the first dimensional capillary.

First dimensional capillary: Width 1.1 mm×length 70 mm×depth 0.4 mm

Second dimensional capillary: Width 1.1 mm×length 60 mm×depth 0.3 mm

Figure 2:
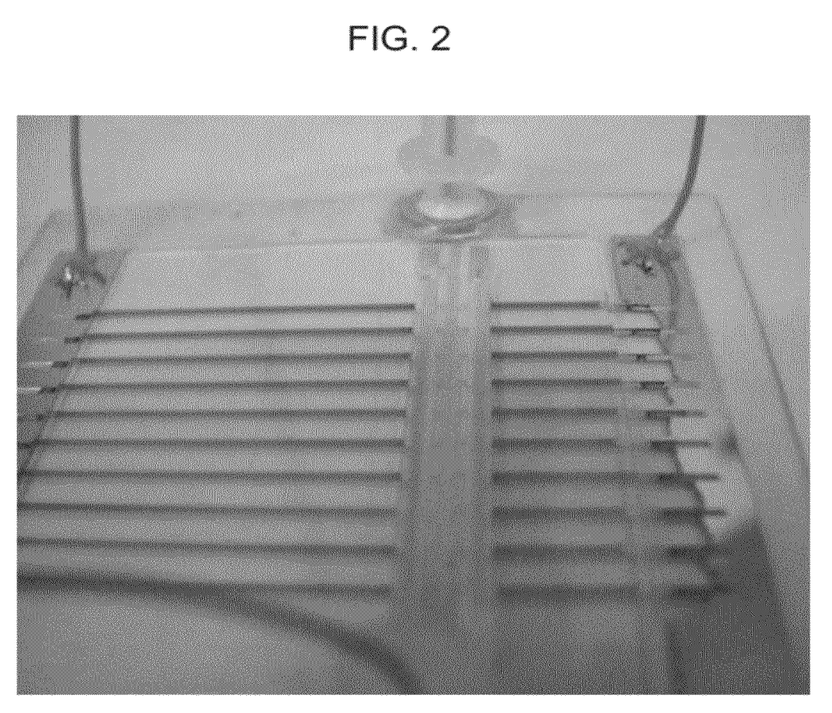
FIG. 2 is a photograph showing the structure of the two-dimensional electrophoretic device produced in the Example.
Figure 3:
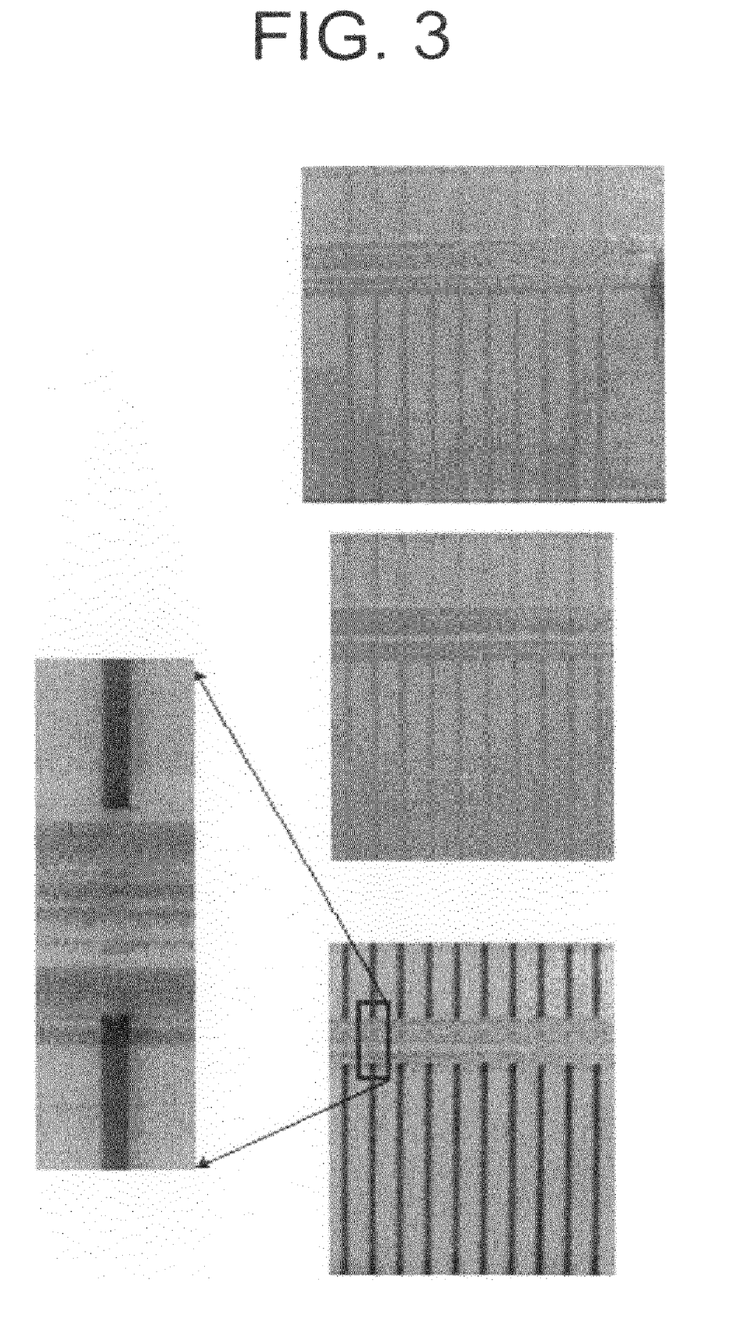
FIG. 3 is photographs showing how the intermediate cavity prevents liquid transfer between the capillaries.

Capillary of the intervening intermediate cavity: Width 2.0 mm×length 50 mm×depth 0.5 mm FIG. 1 shows the structure of the two-dimensional electrophoretic device produced, and FIG. 2 shows a photograph of the same. Such an arrangement enables control of substance transfer to the second dimensional capillaries in either direction. The structure of the intermediate cavity is not a complicated micromachine structure comprising valves or other mechanical components, but rather a groove which can be readily produced. When liquid has not been introduced, the intermediate cavity prevents substance transfer from the intersection to the second dimensional cavity. Due to surface tension there is no movement of the substance to the intermediate cavity at the intersection of the first cavity and the intermediate cavity. FIG. 3 shows how the first and second dimensional capillaries are separated by an intermediate cavity.

When moving the substance to be electrophoresed to a second dimensional cavity after completing the first dimensional isoelectric focusing, electroconductive aqueous solution is introduced to the two capillaries constituting the intermediate cavity. The electroconductive aqueous solution functions as a connection medium. When the capillaries are filled with aqueous solution, the separation medium separating the solution of the first and second dimensions (air) is no longer present, and the solutions are thus in electrical contact. Under these conditions, applying voltage to the second cavity will start second dimensional electrophoresis. In other words, proteins separated in the first dimensional capillary will develop from the intersection nearest to the separation site of each protein, into the electrophoretic medium in the second cavity, via the intermediate cavity.

Aqueous solution is introduced to the capillary solely by capillarity, requiring no mechanical drive. Thus, this introduction can be accomplished extremely easily, reliably, and speedily.

INDUSTRIAL APPLICABILITY

The present invention provides methods for controlling the transfer of fluid substances, and/or substances comprised in fluid substances, by introducing a connection medium. By using the present invention, diffusion into the second dimensional electrophoretic medium can be suppressed during the first dimensional electrophoresis, even in two-dimensional electrophoresis. The methods of the present invention enable substance transfer to be controlled by the introduction of a connection medium to the intermediate cavity. When a buffer is used as the connection medium, substance transfer can be realized by simply introducing a liquid to the intermediate cavity. Accordingly, the present invention provides methods which readily and simply enable substance control.

This invention also provides methods for two-dimensional electrophoresis, and devices for such electrophoresis, based on the methods for controlling substance transfer of the present invention. The methods for two-dimensional electrophoresis of the present invention can be readily implemented on microchips. The present methods can also ensure substance transfer without depending on complicated mechanisms. Protein electrophoresis using microchips will become an important technology, reducing the time required for analysis and enabling proteome analysis based on minute sample amounts.

Please note that all prior art documents referred to herein are incorporated herein by reference.

The invention claimed is:

1. A method for controlling transfer of one or more liquid or solid substances from a first cavity to a second cavity wherein the first cavity is connected to the second cavity by an intermediate cavity, comprising the steps of:
   a) introducing into the first cavity said one or more liquid or solid substances whose transfer is to be controlled, wherein the intermediate cavity is provided with a separation medium comprising a gas or liquid material which prevents transfer of said one or more liquid or solid substances into the intermediate cavity; and
   b) replacing the separation medium in the intermediate cavity with a connection medium comprising a liquid material by delivering said connection medium into the intermediate cavity separately from the first cavity and second cavity, wherein the delivery of said connection medium in the intermediate cavity allows transfer of said one or more liquid or solid substances from the first cavity to the second cavity via the intermediate cavity,
   thereby controlling transfer of one or more liquid or solid substances.

2. The method of claim 1, wherein at least one of the following steps (1) to (3) is carried out in the first and/or second cavity:
   (1) separating said one or more liquid or solid substances by applying a driving force selected from the group consisting of voltage, centrifugal force, capillarity, magnetic force, electroosmotic flow and mechanical pumping;
   (2) reacting said one or more liquid or solid substances; and
   (3) detecting said one or more liquid or solid substances.

3. The method of claim 1, wherein the one or more liquid or solid substances are separated by electrophoresis in the first and/or second cavities.

4. The method of claim 1, wherein the first cavity, the second cavity, and the intermediate cavity comprise a groove or tube configuration; the separation medium is air; and the connection medium is an electroconductive liquid solution, wherein said connection medium is introduced into the intermediate cavity by capillarity.

5. The method of claim 1, wherein said one or more substances whose transfer is to be controlled are liquid; the separation medium is a liquid material immiscible to said one or more liquid substances whose transfer is to be controlled; the connection medium is miscible with the one or more liquid substances whose transfer is to be controlled; and said connection medium is delivered into the intermediate cavity through one or more ports connected to the intermediate cavity separately from the first cavity and second cavity by micropump or electroosmotic flow.

6. A device for controlling transfer of one or more liquid or solid substances, comprising:
- a) a first cavity for holding said one or more liquid or solid substances;
- b) a second cavity for receiving said one or more liquid or solid substances;
- c) an intermediate cavity connecting the first cavity and the second cavity, the intermediate cavity for holding a separation medium comprising a gas or liquid material which prevents transfer of said one or more liquid or solid substances from the first cavity and for receiving and holding a connection medium comprising a liquid which allows transfer of said one or more liquid or solid substances into the intermediate cavity, wherein the intermediate cavity has an inlet and an outlet between the first and second cavities, wherein the inlet and outlet are separate, and
- d) one or more ports connected to the intermediate cavity configured for delivering the connection medium into the intermediate cavity separately from the first cavity and second cavity,
- wherein the separation medium is replaced with a connection medium in the intermediate cavity via the one or more ports, and the delivery of the connection medium to the intermediate cavity enables transfer of said one or more liquid or solid substances retained in the first cavity to the second cavity via the intermediate cavity.

7. The device of claim 6, wherein the first cavity and/or the second cavity comprises at least one of the following mechanisms (1) to (3):
- (1) a mechanism for separating said one or more liquid or solid substances by applying a driving force selected from the group consisting of voltage, centrifugal force, capillarity, magnetic force, electroosmotic flow and mechanical pumping;
- (2) a mechanism for reacting said one or more liquid or solid substances; and
- (3) a mechanism for detecting said one or more liquid or solid substances.

8. The device of claim 6, wherein the intermediate cavity has a width and depth ranging from about 1 to about 2000 μm.

9. The device of claim 8, wherein the intermediate cavity has a width and depth ranging from about 10 to about 100 μm.

10. The device of claim 6, further comprising a plurality of electrodes.

11. The device of claim 6, comprising two or more second cavities.

12. A method for conducting two-dimensional electrophoresis, comprising the steps of:
- a) providing an electrophoretic device comprising:
  - i) a first cavity for holding a first electrophoretic medium;
  - ii) a second cavity for holding a second electrophoretic medium;
  - iii) an intermediate cavity for connecting the first cavity and the second cavity, for holding a separation medium comprising a gas or liquid material which prevents transfer of one or more proteins to be electrophoresed from the first electrophoretic medium to the second electrophoretic medium, and for holding a connection medium comprising a liquid material which allows transfer of said one or more proteins from the first cavity to the second cavity via the intermediate cavity;
  - iv) one or more ports connected to the intermediate cavity configured for delivering the connection medium into the intermediate cavity separately from the first cavity and second cavity, and
  - v) a plurality of electrodes;
- b) introducing one or more proteins to be electrophoresed into the first cavity of the electrophoretic device;
- c) conducting electrophoresis in the first cavity of the electrophoretic device;
- d) replacing a separation medium comprising air by introducing a liquid connection medium into an intermediate cavity through the one or more ports connected to the intermediate cavity, which allows transfer of said one or more proteins to be electrophoresed into the second cavity via the intermediate cavity of the electrophoretic device; and
- e) conducting electrophoresis of said one or more proteins to be electrophoresed in the second cavity of the electrophoretic device.

\* \* \* \* \*